United States Patent
Ito et al.

(10) Patent No.: US 11,607,473 B2
(45) Date of Patent: Mar. 21, 2023

(54) NOTOCHORDAL CELL MATRIX AS A STIMULANT FOR INTERVERTEBRAL DISC REGENERATION

(71) Applicant: Technische Universiteit Eindhoven, Eindhoven (NL)

(72) Inventors: Keita Ito, Helmond (NL); Stefan Antonius Henricus de Vries, Veldhoven (NL)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 411 days.

(21) Appl. No.: 16/068,752

(22) PCT Filed: Jan. 10, 2017

(86) PCT No.: PCT/EP2017/050431
§ 371 (c)(1),
(2) Date: Jul. 9, 2018

(87) PCT Pub. No.: WO2017/121736
PCT Pub. Date: Jul. 20, 2017

(65) Prior Publication Data
US 2019/0022278 A1 Jan. 24, 2019

Related U.S. Application Data

(60) Provisional application No. 62/277,032, filed on Jan. 11, 2016.

(51) Int. Cl.
| | | |
|---|---|---|
| *A61L 27/36* | (2006.01) | |
| *A61K 9/00* | (2006.01) | |
| *A61K 35/12* | (2015.01) | |
| *A61K 35/30* | (2015.01) | |

(52) U.S. Cl.
CPC ........ *A61L 27/3608* (2013.01); *A61K 9/0085* (2013.01); *A61K 35/12* (2013.01); *A61K 35/30* (2013.01); *A61L 27/3604* (2013.01); *A61L 27/365* (2013.01); *A61L 27/3658* (2013.01); *A61L 27/3683* (2013.01); *A61L 27/3691* (2013.01); *A61L 2430/38* (2013.01)

(58) Field of Classification Search
None
See application file for complete search history.

(56) References Cited

U.S. PATENT DOCUMENTS

| | | | | |
|---|---|---|---|---|
| 6,723,335 | B1 * | 4/2004 | Moehlenbruck | A61L 27/50 424/425 |
| 2009/0202653 | A1 | 8/2009 | Erwin et al. | |
| 2012/0045419 | A1 | 2/2012 | Erwin et al. | |
| 2016/0015753 | A1 | 1/2016 | Temple | |
| 2016/0235892 | A1 | 8/2016 | Detamore et al. | |
| 2019/0022145 | A1 | 1/2019 | O'Heeron | |
| 2019/0022278 | A1 | 1/2019 | Ito et al. | |

FOREIGN PATENT DOCUMENTS

| | | |
|---|---|---|
| WO | WO2002081660 | 10/2002 |
| WO | WO2015048317 | 4/2015 |
| WO | 2017/121736 A1 | 7/2017 |
| WO | 2017/123951 A1 | 7/2017 |

OTHER PUBLICATIONS

Mercuri et al. "Novel tissue-derived biomimetic scaffold for regenerating the human nucleus pulposus." Journal of biomedical materials research Part A 96.2 (2011): 422-435. (Year: 2011).*
Illien-Junger et al. "Development of a bovine decellularized extracellular matrix-biomaterial for nucleus pulposus regeneration." Journal of Orthopaedic Research 34.5 (2016): 876-888 (Year: 2016).*
Yuan et al. "Effects of nucleus pulposus cell-derived acellular matrix on the differentiation of mesenchymal stem cells." Biomaterials 34.16 (2013): 3948-3961 (Year: 2013).*
Illien-Jünger et al. "Development of a bovine decellularized extracellular matrix-biomaterial for nucleus pulposus regeneration." Journal of Orthopaedic Research 34.5 (published online Dec. 1, 2015): 876-888 (Year: 2015).*
Risbud et al. "Notochordal cells in the adult intervertebral disc: new perspective on an old question." Critical Reviews™ in Eukaryotic Gene Expression 21.1 (2011). (Year: 2011).*
Liu et al. "CD24 identifies nucleus pulposus progenitors/notochordal cells for disc regeneration." Journal of Biological Engineering 12.1 (2018): 1-15. (Year: 2018).*
Liu et al. Modulating Notochordal Differentiation of Human Induced Pluripotent Stem Cells Using Natural Nucleus Pulposus Tissue Matrix. PLoS One. 2014; 9(7): e100885. Jul. 23, 2014. doi: 10.1371/journal.pone.0100885.
Wachs et al. Creation of an injectable in situ gelling native extracellular matrix for nucleus pulposus tissue engineering. The Spine Journal 2016 http://dx.doi.org/10.1016/j.spinee.2016.10.022.
Mercuri et al. Novel tissue-derived biomimetic saffold for regenerating the human nucleus pulposus. J. Biomedical Materials Research Part A, vol. 96A(2) Dec. 8, 2010 pp. 422-435.
Sep. 15, 2021 Office Action issued in U.S. Appl. No. 16/261,771.
May 9, 2019 International Search Report issued in International Patent Application No. PCT/EP2019/052304.
May 9, 2019 Written Opinion issued in International Patent Application No. PCT/EP2019/052304.

(Continued)

*Primary Examiner* — Emily A Cordas
(74) *Attorney, Agent, or Firm* — Oliff PLC (57) ABSTRACT

A solubilized notochordal cell matrix powder dissolved in a carrier solvent or formed as a gel is provided. The notochordal cell matrix powder originates from lyophilized and treated porcine nucleus pulposus tissue containing notochordal cells. The powder contains less than 20% of porcine nucleid acids, and the powder contains a substantially unchanged amount of porcine protein content compared to the originating porcine nucleus pulposus tissue. The solubilized notochordal cell matrix powder is capable of stimulating native or stem cells to proliferate and produce a significant increase inglycosaminoglycansand type-II collagen matrix. Embodiments of the invention can be used for the disc regenerative treatment of discogenic back and neck pain in an orthopaedic and/or pharmaceutical setting/approach.

3 Claims, 9 Drawing Sheets

(56) References Cited

OTHER PUBLICATIONS

Apr. 1, 2021 Office Action issued in U.S. Appl. No. 16/261,7/1.
Apr. 6, 2017 Written Opinion issued in International Patent Application No. PCT/EP2017/050431.
Apr. 6, 2017 International Search Report issued in International Patent Application No. PCT/EP2017/050431.
U.S. Appl. No. 16/261,771, filed Jan. 30, 2019 in the name of Keita Ito et al.
U.S. Appl. No. 16/965,046, filed Jul. 27, 2020 in the name of Keita Ito et al.
Kwon et al., "Injectable Extracellular Matrix Hydrogel Developed Using Porcine Articular Cartilage," International Journal of Pharmaceutics, vol. 454, No. 1, pp. 183-191, Sep. 15, 2013.
Nov. 14, 2022 Office Action Issued In U.S. Appl. No. 16/965,046.

* cited by examiner

NOTOCHORDAL CELL MATRIX AS A STIMULANT FOR INTERVERTEBRAL DISC REGENERATION

CROSS-REFERENCE TO RELATED APPLICATIONS

This application is a 371 of PCT/EP2017/050431 filed Jan. 11, 2017. PCT/EP2017/050431 claims the benefit of U.S. Provisional Application 62/277032 filed on Jan. 11, 2016.

FIELD OF THE INVENTION

This invention relates to intervertebral disc regeneration.

BACKGROUND OF THE INVENTION

Low back pain as a result of intervertebral disc (IVD) degeneration is a common condition with a high impact on society, physically for the afflicted individual, as well as economically.

Current treatment methods for degeneration-induced low back pain are fusion, and total disc replacement. Both methods are somewhat successful in alleviating low back pain, but do not have a sufficiently high clinical efficacy and are too often accompanied by complications. Furthermore, disc prostheses are inherently of limited longevity. Ultimately, it is desired to restore a degenerating disc to a healthy state, i.e. regeneration. Unfortunately, this is not straightforward, requires biologically active intervention and has so far been unsuccessful. The present invention advances the art and introduces notochordal cell matrix as a stimulant for intervertebral disc regeneration.

Prior to skeletal maturity, our discs are healthy and filled by a central nucleus pulposus (NP) tissue rich in notochordal cells (NCs). By age 10, we lose these NCs and thereafter our discs contain mostly chondrocyte-like cells, named nucleus pulposus cells (NPCs). About a decade or two after we lose our NCs, our discs start to degenerate with age. Other species, e.g. pigs, keep their NCs even as adults. Their IVDs do not degenerate. Hence, we believe that NCs help to maintain a healthy IVD by producing soluble factors. We further believe that these factors are present in the extracellular matrix of NC-rich NP tissue, and our invention is to use the matrix from NC-rich NP to directly stimulate degenerated IVDs to repair and regenerate.

SUMMARY OF THE INVENTION

The present invention provides a method of making a notochordal cell matrix solution or gel for the purposes of regenerating the intervertebral disc. In addition, the invention provides an intervertebral disc regeneration stimulant processed by the method as described.

First, porcine nucleus pulposus tissue containing notochordal cells is lyophilized to destroy cells within the tissue and to make a dry and brittle tissue. Second, the dry and brittle tissue is treated by DNAse, RNAse, detergent, or a combination thereof (e.g. benzonase & TRITON™ detergent) to remove cellular and nucleic acid remnants. This treatment results in at least 80% removal of porcine nucleic acids from the porcine nucleus pulposus tissue, while substantially maintaining porcine protein content within the porcine nucleus pulposus tissue. In a different way of saying, the treatment results in the material containing less than 20% of porcine nucleic acid, and containing a substantially unchanged amount of porcine protein content compared to the originating porcine nucleus pulposus tissue.

The order of first lyophilization followed by nucleic acid removal is important to achieve this result. Porcine genomic material harbors endogenous retroviruses (PERVs). PERVs do not come to expression in the pig itself, but may become active upon implantation in different species, e.g. human. Hence, removal of genomic material to minimize the risk of disease transmission is an important step prior to its application in a regenerative therapy.

In the case of removal of nucleic acids from NP tissue, either in a wet state or after disintegration, which is different from the present invention, such treatment has resulted in the removal of more than 90% of the nucleic acid content but also at a considerable loss of extracellular matrix proteins (>40%). The present invention teaches the substantial removal of nucleic acid from porcine NP tissue, while largely or substantially maintaining its protein content (e.g. active factors).

Third, the treated material is further lyophilized and pulverized into a notochordal cell matrix powder. The notochordal cell matrix powder is solubized by dissolving the notochordal cell matrix powder in a carrier solvent or formed as a gel.

The solubilized notochordal cell matrix powder is capable of stimulating native or stem cells to proliferate and produce a substantial increase in glycosaminoglycans and type-II collagen matrix.

The solubilized notochordal cell matrix powder is capable of stimulating native or stem cells to proliferate and produce a significant increase in glycosaminoglycans. In one example, the solubilized notochordal cell matrix powder is capable of stimulating native or stem cells to proliferate and produce an at least a multi-fold (e.g. at least two to three times) increase in glycosaminoglycans. In another example, the solubilized notochordal cell matrix powder is capable of stimulating native or stem cells to proliferate and produce an at least a seven times increase in glycosaminoglycans. In general, the increase depends on the species, the dosage of powder administered and whether it is administered in-vitro or in in-vivo.

The intervertebral disc regeneration stimulant solution or gel is defined as a solubilized notochordal cell matrix powder dissolved in a carrier solvent or formed as a gel, whereby the notochordal cell matrix powder originates from lyophilized and treated porcine nucleus pulposus tissue containing notochordal cells. The powder contains less than 20% of porcine nucleic acid, and the powder contains a substantially unchanged amount of porcine protein content compared to the originating porcine nucleus pulposus tissue.

Embodiments of the invention have the following advantages:

Porcine notochordal nucleus puposus tissue is plentiful.
Porcine notochordal nucleus puposus tissue can be easily processed following the described steps, supra, to produce a powder that is not harmful and which can stimulate IVD regeneration.
By using notochordal cell matrix powder, the difficult and time-consuming step to identify and produce the specific soluble active factors secreted by notochordal cells is unnecessary.
The solubilized notochordal cell matrix powder can be injected into the IVD through a small gage needle (<27 G) causing minimal harm to its outer annulus fibrosus.
The solubilized notochordal cell matrix powder forms a self-assembling hydrogel at higher concentrations, may be used as a (stem) cell carrier, to replenish the decreasing cell number that characterizes intervertebral disc degeneration.

The solubilized notochordal cell matrix powder is sufficient, on its own, to induce stem cells to become NPCs.

The solubilized notochordal cell matrix powder at higher concentrations has rheological properties similar to the natural nucleus pulposus. Thus, it can replenish and easily integrate into the nucleus pulposus tissue.

The solubilized notochordal cell matrix powder at higher concentrations has considerable swelling potential. Thus it can add swelling pressure to the nucleus pulposus.

The solubilized notochordal cell matrix powder can be combined with suitable carriers, creating a sustained release of its soluble components and therefore a longer-lasting regenerative effect.

BRIEF DESCRIPTION OF THE DRAWINGS

FIG. 5 shows according to an exemplary embodiment of the invention as an instructive stem cell carrier. The left panel is a live/dead cell staining with calcein-AM and propridium iodide of human bone marrow stromal cells (MSCs) mixed in 20% w/vol solubilized notochordal cell matrix powder, injected through a 27 G needle and subsequently cultured in base medium (24 hrs). The right panel are Safranin O stained thin histology sections of MSC pellet cultures (4 weeks) in base medium (control), base medium plus 10 ng/ml TGF/β1 (+TGFβ1) or base medium plus 10 mg/ml solubilized notochordal cell matrix powder (+NCM). After injection in NCM, MSCs remain viable (solid & hollow arrows). Within 24 hr, they attach to the NCM forming a more spindle shape (hollow arrows). NCM stimulates MSC to proliferate (larger cell mass) and assume a chondrogenic phenotype producing a matrix rich in GAGs (Safranin O=lighter stain).

FIGS. 6A-C show according to an exemplary embodiment of the invention the rheology and osmotic properties of the solubilized notochordal cell matrix powder: FIG. 6A) storage (G') and loss (G") modulus and FIG. 6B) phase shift (tan δ) frequency sweep of bovine young adult nucleus pulposus tissue (NP) and 10, 20 and 30% w/vol solubilized notochordal cell matrix powder (NCM); FIG. 6C) osmotic pressure as function of solubilized notochordal cell matrix powder concentration (% w/vol, NCM gel) calculated from swelling against various concentration polyethylene glycol solutions (analysis method as outlined in NO Chahine, et al. Biophys J, 89(3):1543-1550, 2005). The rheological properties of NCM, especially at higher concentrations approach that of natural nucleus pulposus tissue. At concentrations greater than 15% w/vol, NCM has enough osmotic potential to restore tonicity to nucleus pulposus tissue whose own natural osmotic potential is 0.1-0.2 MPa.

DETAILED DESCRIPTION

According to an embodiment of the invention, healthy NC-rich NP tissue is harvested, e.g. from porcine spines. The tissue is then lyophilized, thereby destroying the cells, and leaving behind a dry brittle tissue. Benzonase, DNAse, RNAse, detergent, or a combination thereof is then used to remove the cellular and nucleic acid remnants, after which the tissue is lyophilized again. The brittle tissue is then pulverized to a fine powder. This powder can be dissolved in a carrier solvent like PBS, a viscous carrier like hyaluronic acid or even a sustained release hydrogel or microspheres, and injected into the IVD to stimulate intervertebral disc regeneration. According to the invention, the dissolved and directly injected powder has the ability to promote healthy matrix production and inhibit inflammation. Additionally, it may inhibit matrix catabolism, inhibit neovascularization and inhibit neo-innervation within the IVD.

Exemplary Embodiment and Results

An experiment was performed to test whether the powdered NC-rich NP tissue Matrix (NCM) has a stimulatory effect and how similar this is to just proteins produced by NC cells, i.e. NC Conditioned Medium (NCCM).

NCCM was produced by incubating porcine NC-rich NP tissue for 4 days in high glucose DMEM with 1% penicillin/streptomycin (p/s) at 37° C., 5% $CO_2$ and 5% $O_2$. Afterwards, the medium was poured through a 70 μm strainer to remove the NCs and tissue. Subsequently, it was filtered through a 3 kDa filter, the solutes that remained where resuspended in low glucose (1 g) DMEM, and the NCCM was stored at −80° C.

NCM was produced by lyophilizing porcine NP tissue overnight after which it was ground to a fine powder. The protein content of both NCCM and NCM was measured so that when NCM was resuspended in low glucose (1 g) DMEM, the final protein concentrations of both were the same.

These (NCM and NCCM) were compared to base medium (BM=1 gDMEM supplemented with ITS, ascorbic acid, L-proline, bovine serum albumin and p/s).

Cells, similar to those in human adult discs, i.e. NPCs, were harvested from the caudal discs of bovine tails by enzymatic digestion, and seeded in 1.2% alginate beads at 3 million cells/ml alginate. The beads were cultured for 4 weeks in BM, NCCM or NCM (both with the same supplements as BM).

After culture, the beads were analysed for glycosaminoglycan (GAG) and DNA content (directly correlated to cell number). GAG is the main ECM component of NP tissue, it gives the NP tissue its functional mechanical properties and it is the first to be decreased during IVD degeneration.

Figure 1A:
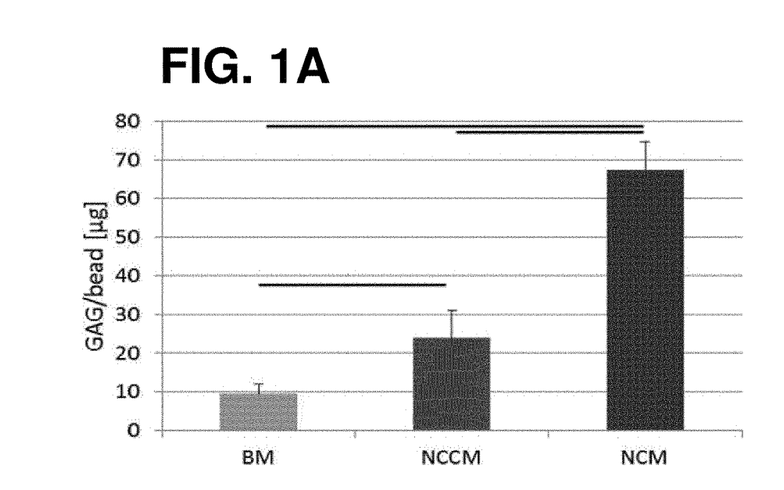
FIGS. 1A-C shows according to exemplary embodiments of the invention the biochemical content expressed as glycosaminoglycan (GAG) in FIG. 1A, DNA in FIG. 1B, and GAG per DNA in FIG. 1C of NPCs embedded in alginate beads, treated with base medium (BM), base medium plus soluble factors from medium conditioned with notochordal cell tissue culture (NCCM), or base medium plus solubilized notochordal cell matrix powder (NCM) in culture for 4 weeks. NCM not only stimulates cells to proliferate, but also each cell to produce more GAG resulting in almost a 7× overall increase in GAG production.
Figure 1B:
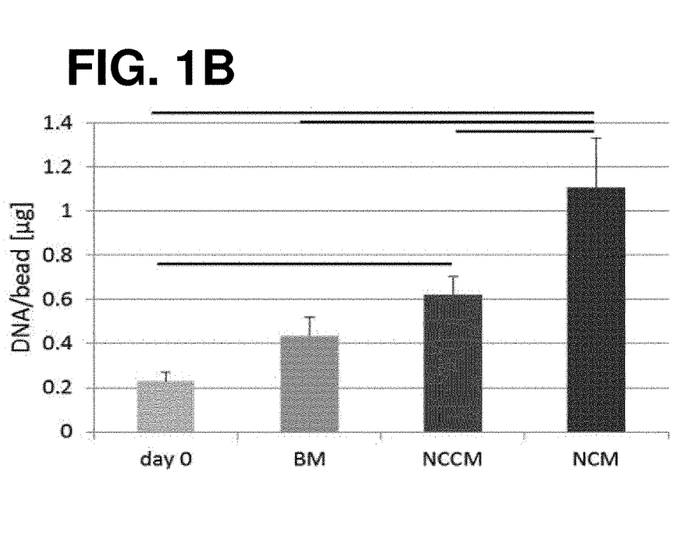

As observed previously, just the proteins derived from NCs (NCCM) caused the disc cells to proliferate 1.3× compared to BM (FIG. 1B). It also stimulated each cell to produce 1.8× more GAG than those cultured without the added proteins (BM, FIG. 1C). These two mechanisms combined resulted in an overall increase in GAG content that was a little over 2× with the NC proteins (NCCM) than without (BM, FIG. 1A).

Figure 1C:
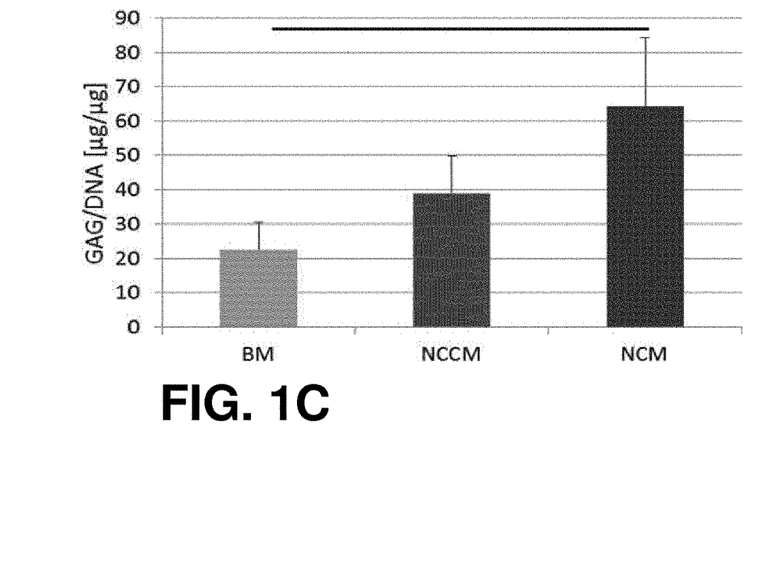

With the powdered NC-matrix added to the medium (NCM), the cells proliferated almost 5× more than without (BM, FIG. 1B), and stimulated each cell to produce 3× more GAG (FIG. 1C). Thus, the overall increase in stimulated GAG content was 7× greater with the NC-matrix powder than without (NCM vs BM, FIG. 1A). This superior stimulation of GAG production by NP-matrix powder (NCM) as compared to just the proteins from NCs (NCCM) was unexpected and surprising, suggesting that either presentation of the NC-derived proteins or a synergistic effect combining the proteins with the NC-matrix provides a greater anabolic effect on cells in the center of our discs.

Figure 2:
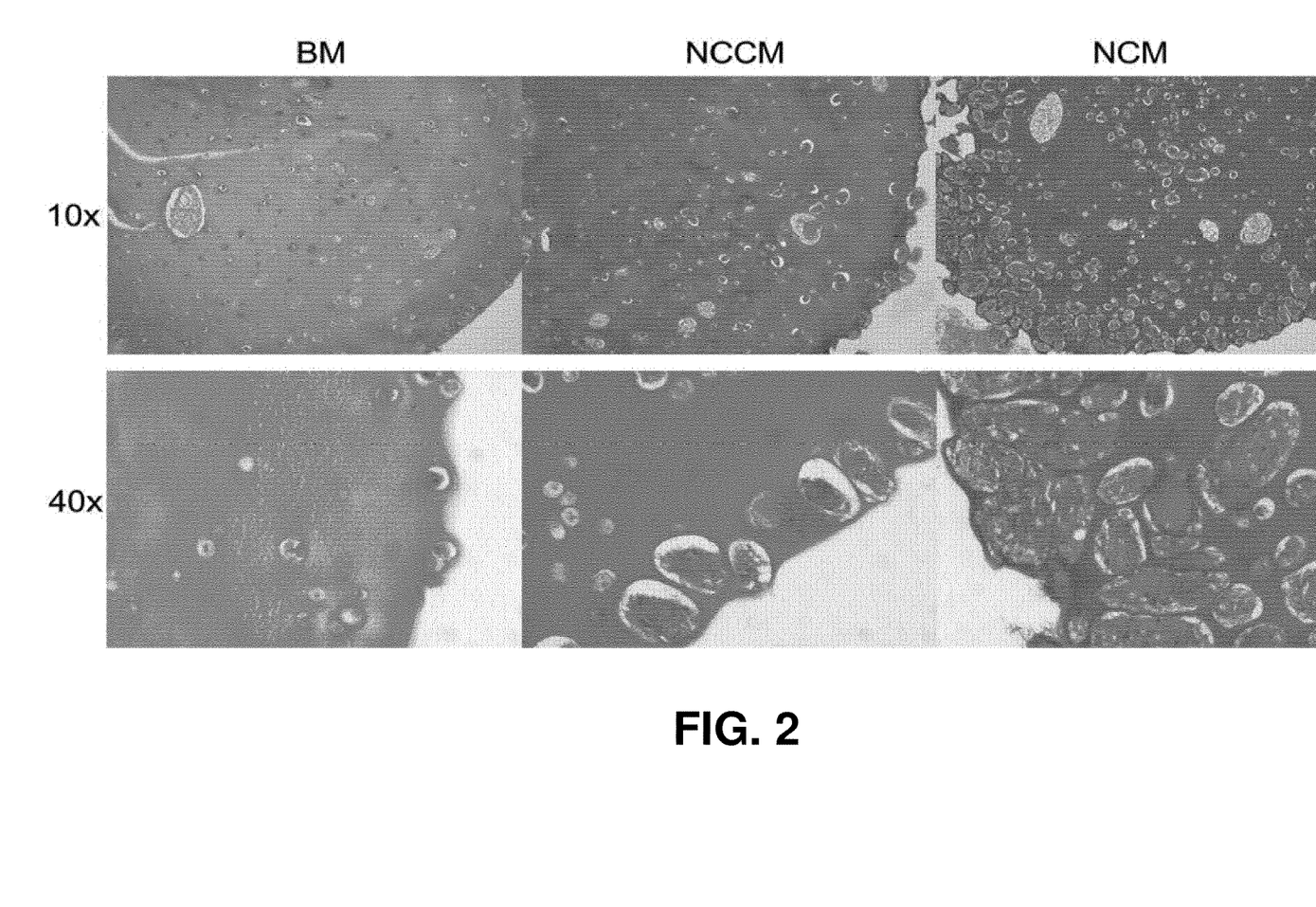
FIG. 2 shows according to exemplary embodiments of the invention alcian blue staining of base medium (BM), base medium plus soluble factors from medium conditioned with notochordal cell tissue culture (NCCM), or base medium plus solubilized notochordal cell matrix powder (NCM) treated NPC embedded alginate beads cultured for 4 weeks, at 10× and 40× magnification. Darker homogenous staining of NCM exposed beads indicated increased and well distributed GAG production. The increased proliferation of cells in clusters with NCM is also demonstrated.
Figure 3:
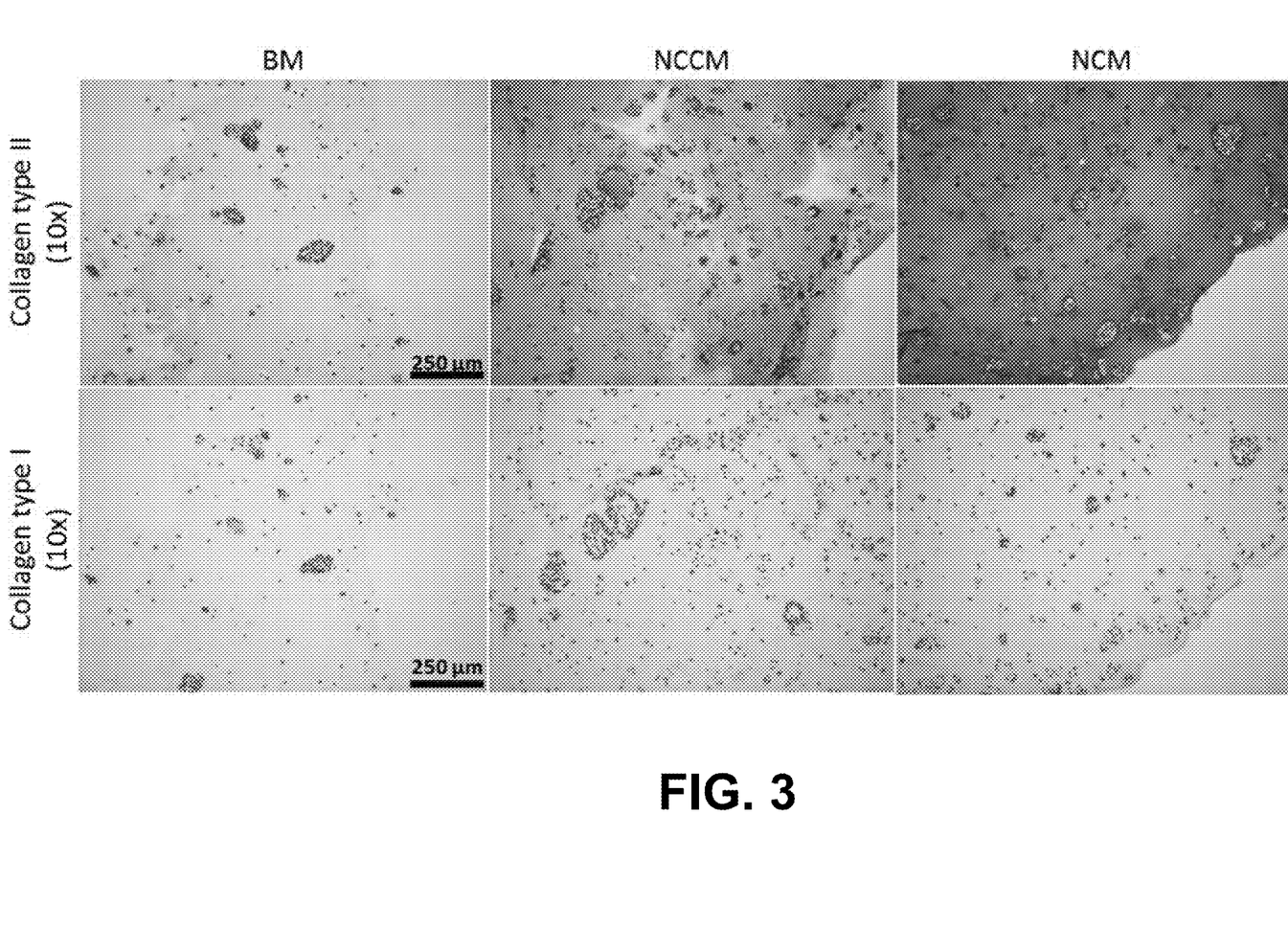
FIG. 3 shows according to exemplary embodiments of the invention collagen type I and type II immunohistochemical staining of NPCs embedded in alginate beads, treated with base medium (BM), base medium plus soluble factors from medium conditioned with notochordal cell tissue culture (NCCM), or base medium plus solubilized notochordal cell matrix powder (NCM) in culture for 4 weeks. As indicated by darker staining, NCM hardly induce any production of type I collagen but was a very strong stimulant for type II collagen.
Figure 4A:
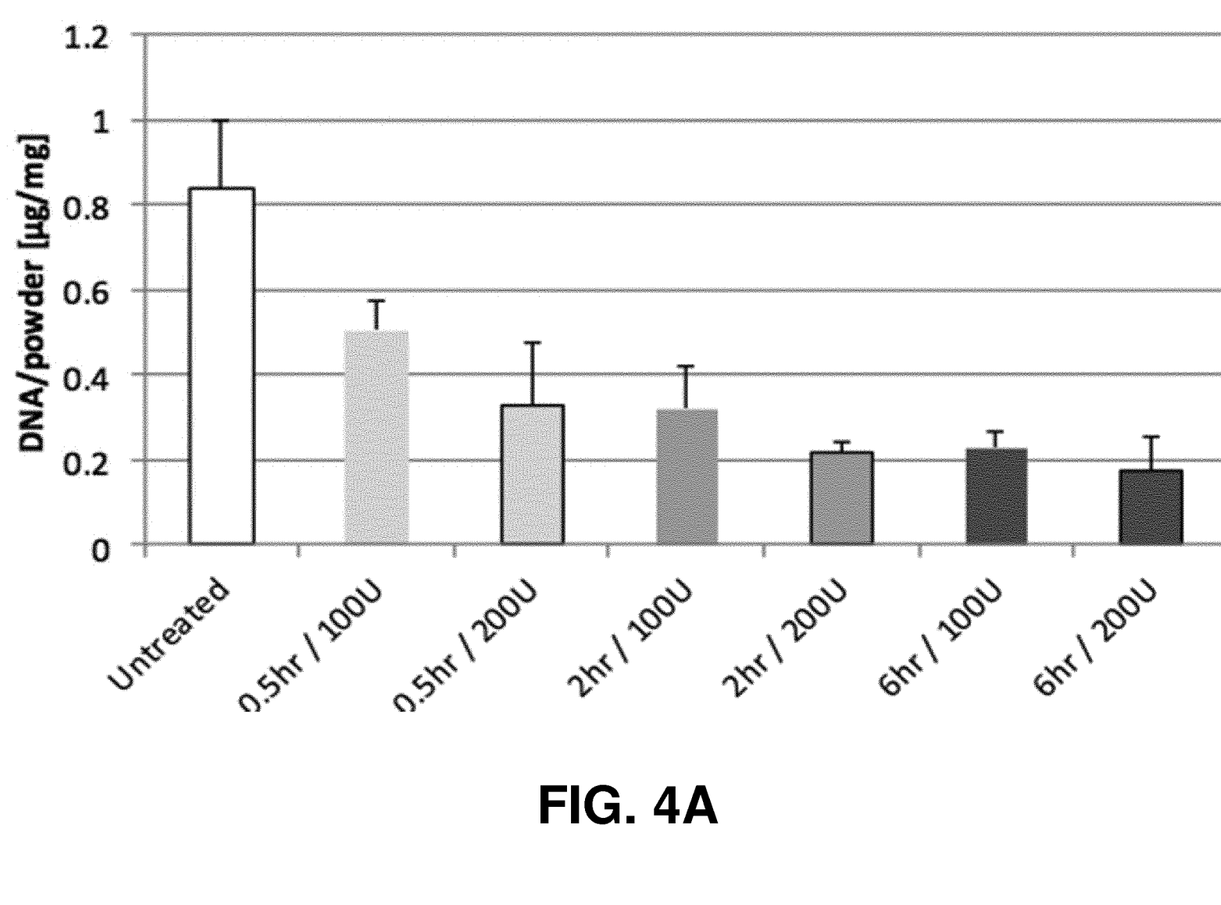
FIGS. 4A-B shows according to exemplary embodiments of the invention in FIG. 4A DNA and in FIG. 4B protein content in untreated and benzonase-treated solubilized porcine notochordal cell matrix powder, where "hr" denotes exposure duration to benzonase and "U" to the benzonase concentration in IU/ml. After treatment for 6 hr with 100 or 200 IU/ml benzonase only 20% of the porcine DNA remained in the NCM while the majority of the protein remained.
Figure 4B:
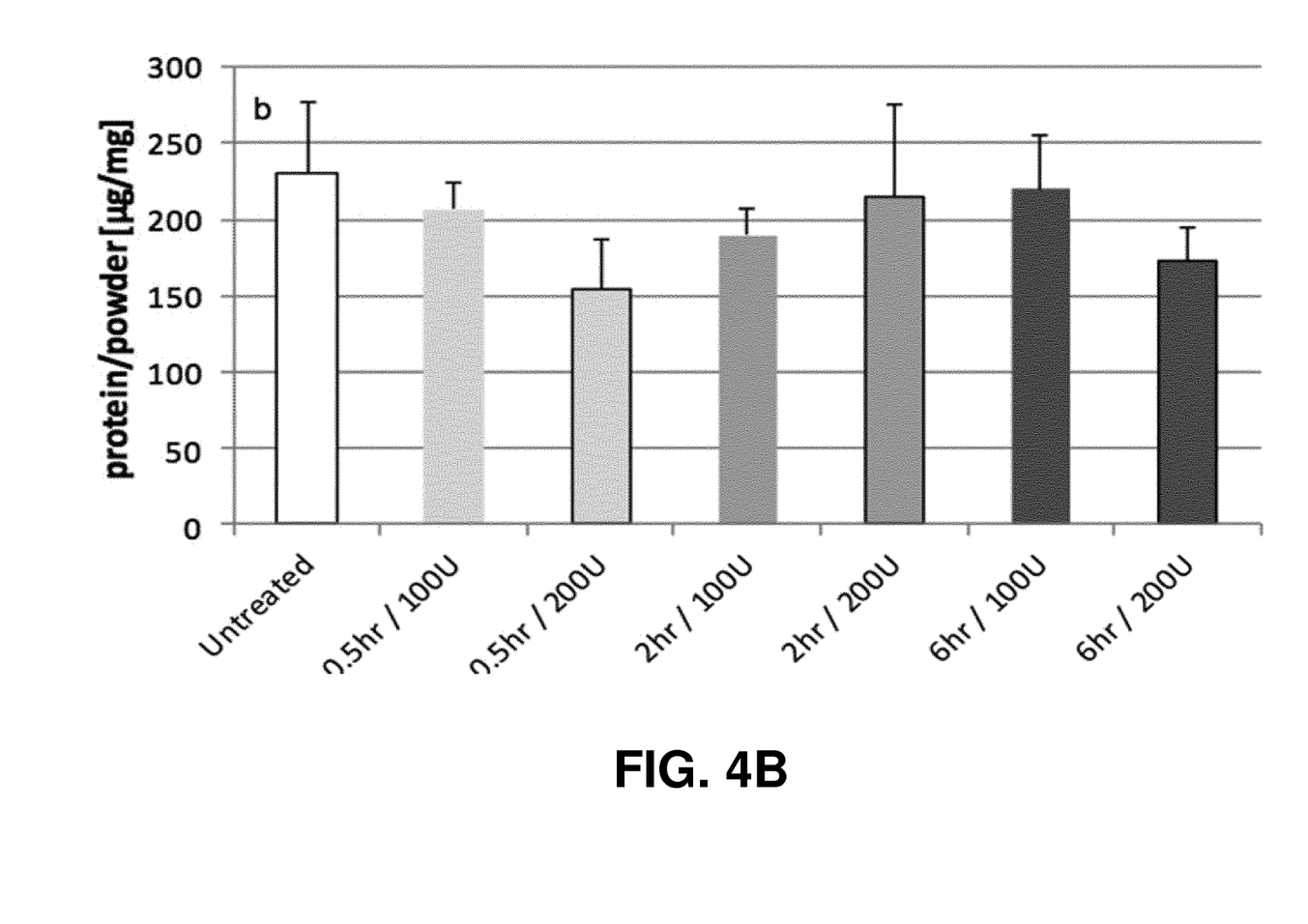

The results from the biochemical assays were also confirmed histologically on Alcian blue stained sections (FIG. 2), where darker blue in NCCM and especially NCM indicates a higher GAG content. At 40× magnification, an increased cell number is observed in NCM compared to NCCM and especially BM.

In vitro experiments have been conducted to further assess the feasibility of NC-matrix powder in intervertebral disc regeneration. NCCM has been demonstrated to have anti-some catabolic and anti-inflammatory effect on inflammation-induced NPCs. Furthermore, NCCM has been shown to inhibit neurite growth and blood vessel formation. We expect the NCM to have similar or better effects than NCCM.

Pigs harbor endogenous retroviruses (PERVs) in their genome, which are able to infect human cells. Therefore, before clinical application becomes feasible, NC-matrix powder (NCM) needs to be decellularized, while maintaining a high as possible protein content. Decellularization is performed with benzonase, which cleaves DNA and RNA to small fragments that can afterwards be removed through washing steps.

A test was performed to remove DNA from NCM. Again, NCM was produced by lyophilizing and grinding porcine NC-rich NP tissue (n=3). The powder was then incubated on a shaker at 37° C. with 2 different concentrations of benzonase (100 U/ml and 200 U/ml) in Tris-EDTA buffer, up to 3 different timepoints (30 min, 2 hrs or 6 hrs). Afterwards, the samples were washed twice with PBS, and the untreated powder, as well as each of the treatment groups, was assayed for DNA and protein content. DNA content decreased with duration of benzonase treatment, and small differences were observed between the two benzonase concentrations. Although some variations in protein content were observed between treatment groups, there were no clear trends for decreasing protein content with treatment time or benzonase concentration. Altogether, these results indicate that it is possible to remove DNA from the NCM, while largely maintaining the protein content.

Once the effects of NC-matrix powder on vessel- and neurite formation, as well as its anti-inflammatory effects have been established, in vivo animal experiments will be performed. If successful, NC-matrix powder could be tested in clinical trials.

In vitro experiments with bovine NPCs used ~2 mg NCM/6*$10^5$ NPCs. This resulted in a strong increase in GAG production as well as cell proliferation. Based on work with Beagle's thoracic NP tissue and bovine caudal NP tissue, we expect the weight of the Beagle's lumbar NP tissue to be ~100 mg, containing ~2*$10^5$ NPCs. Hence, the NCM dosage range that will therefore be tested in a canine in vivo model will be 1 mg, 5 mg, 10 mg and 20 mg NCM per 100 mg NP tissue. Because bio-availability will be affected by the tissue, organ and injection method and cell response in vivo may be different to in vitro, a broad dosage range should be explored. When translating from the canine to human, the exact interspecies differences are also unknown and we speculate that dosages for the human may be +/− one order of magnitude different. For example these could be as broad as 0.1 to 100 mg NCM powder to every 100 mg NP tissue of the human disc.

Embodiments of the invention can be used for the disc regenerative treatment of discogenic back and neck pain in an orthopaedic and/or pharmaceutical setting/approach.

In another embodiment, the notochordal cell matrix (NCM) is a hydrogel. In a concentrated form, 10 to 30% w/vol, the NCM behaves like a loose self-assembling hydrogel that can be injected through a hypodermic needle.

In yet another embodiment, the NCM can be used as a cell carrier. When mixed and injected through a 27 G needle, human bone marrow stromal cells (hBMSCs) maintain their viability (0 hr, rounded form) and thereafter even attach to the matrix components of the NCM hydrogel (spindle form, FIG. 5).

Figure 5:
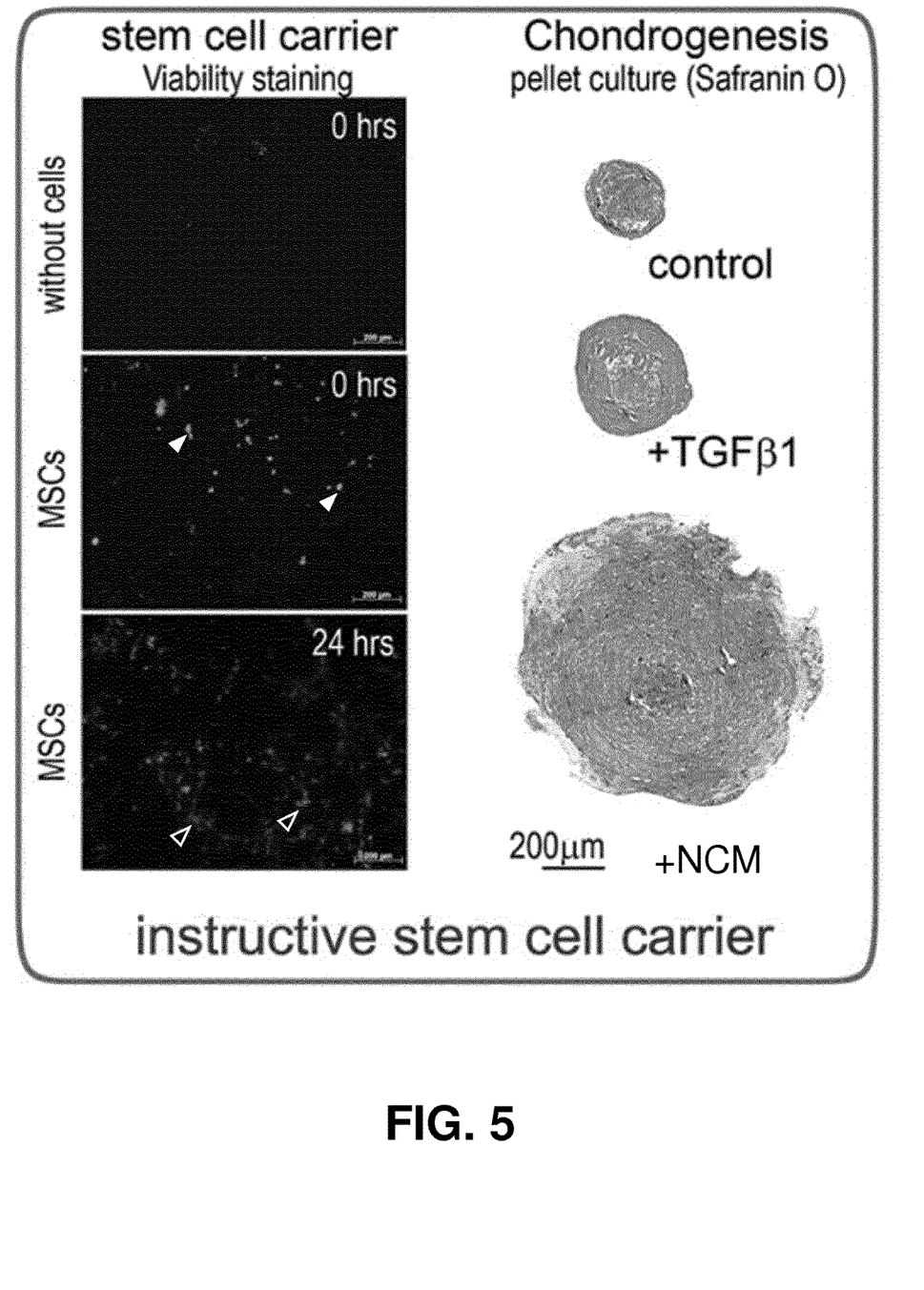

In still another embodiment, the NCM can be progenitor cell instructive. When progenitor cells (hBMSCs) in pellet culture are exposed to NCM (10 mg/ml) in a 4 week culture, they are instructed to differentiate into chondrogenic cells producing a matrix rich in proteoglycans and collagen type-II (FIG. 5).

Figure 6A:
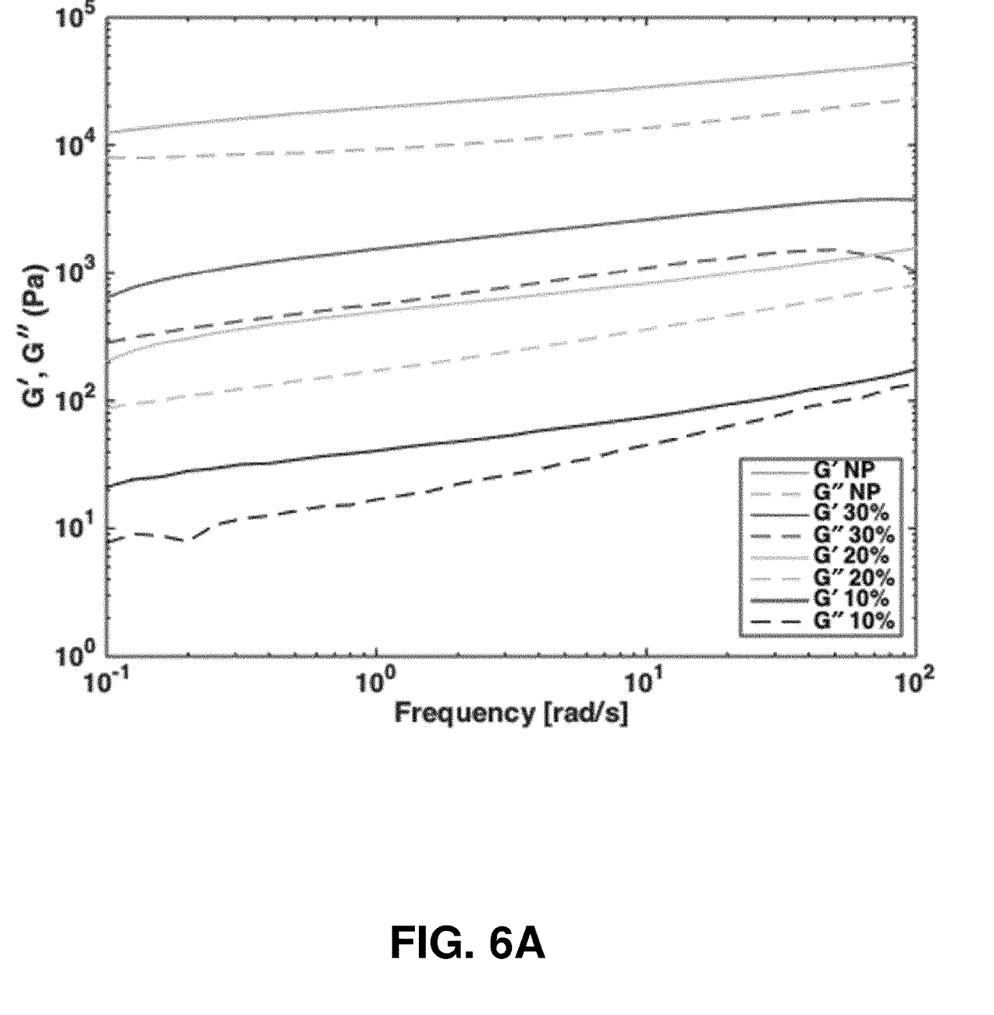
Figure 6B:
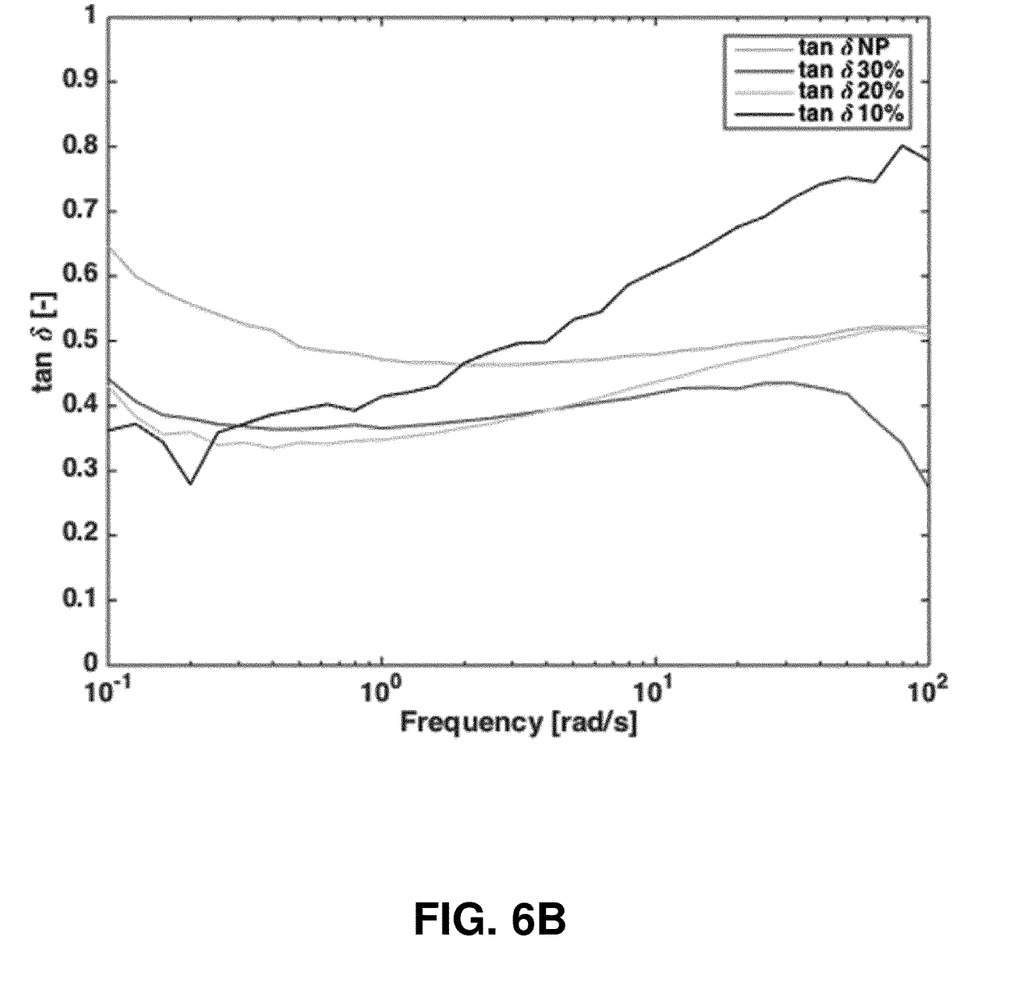
Figure 6C:
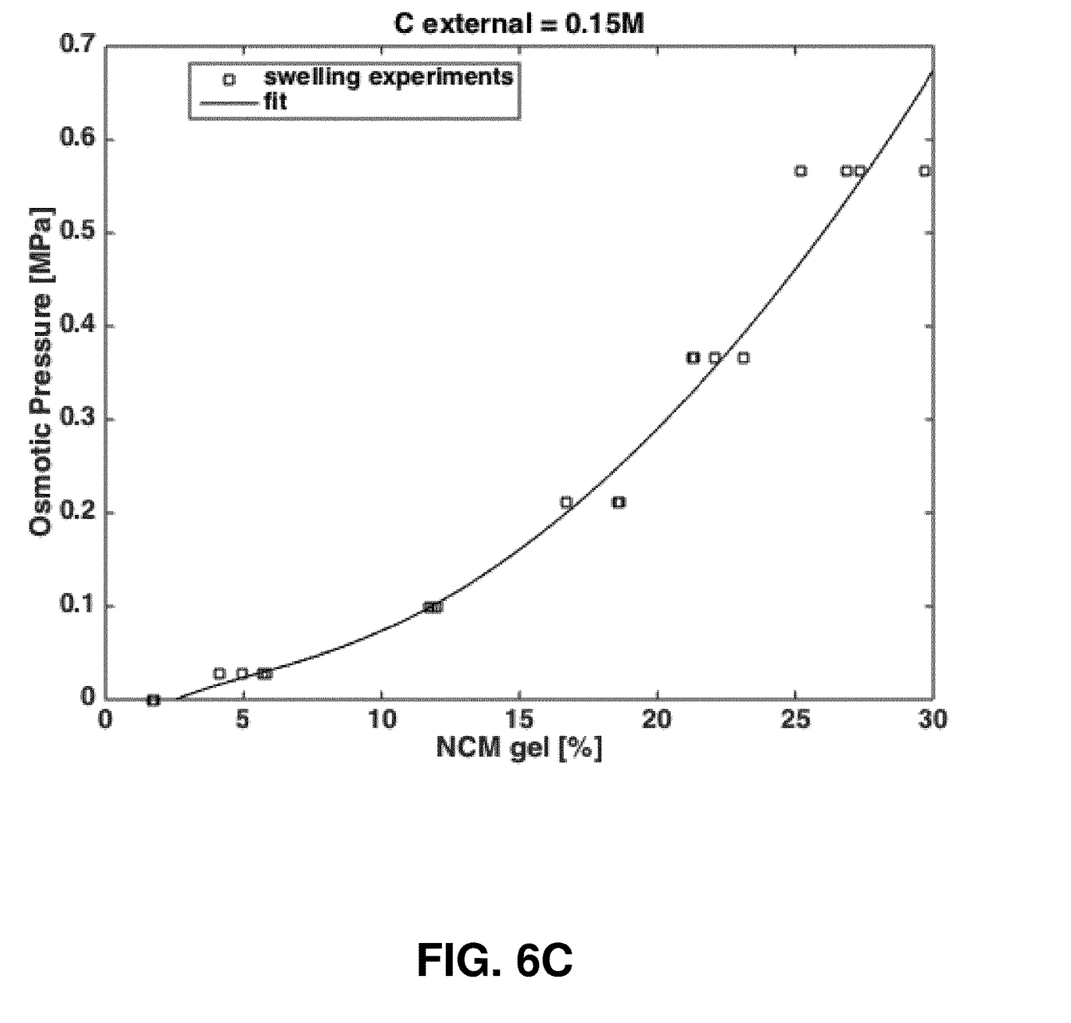

In still another embodiment, the NCM has material properties, which can help to restore the biomechanical characteristic of the IVD to a healthy state. The NCM has rheological properties that are concentration dependent and that at higher concentrations start to approach that of the natural NP tissue (FIGS. 6A-B). NCM also has considerable osmotic swelling potential (FIG. 6C), which can help to directly restore the swelling properties of glycosaminogycan (GAG) depleted moderately degenerated discs.

What is claimed is:

1. A method of making a notochordal cell matrix solution or gel for purposes of regenerating intervertebral disc, comprising:
   (a) lyophilizing porcine nucleus pulposus tissue containing notochordal cells to destroy cells within the tissue and to make a dry and brittle tissue;
   (b) treating the dry and brittle tissue to remove cellular and nucleic acid remnants, wherein the treatment results in at least 80% removal of porcine nucleic acids from the porcine nucleus pulposus tissue while maintaining porcine protein content within the porcine nucleus pulposus tissue;

(c) further lyophilizing the treated material and pulverizing the treated material into a notochordal cell matrix powder; and (d) solubilizing the notochordal cell matrix powder by dissolving the notochordal cell matrix powder in a carrier solvent or forming as a gel, wherein the solubilized notochordal cell matrix powder is capable of stimulating native or stem cells to proliferate and produce an increase in glycosaminoglycans and type-II collagen matrix.

2. The method as set forth in claim 1, wherein the solubilized notochordal cell matrix powder is capable of stimulating the native or stem cells to produce an at least a multi-fold increase in the glycosaminoglycans.

3. The method as set forth in claim 1, wherein the notochordal cell matrix powder is formed into a hydrogel, and the notochordal cell matrix is in a concentration in a range of 10 to 30% w/vol in the hydrogel.

\* \* \* \* \*